Figure 1:
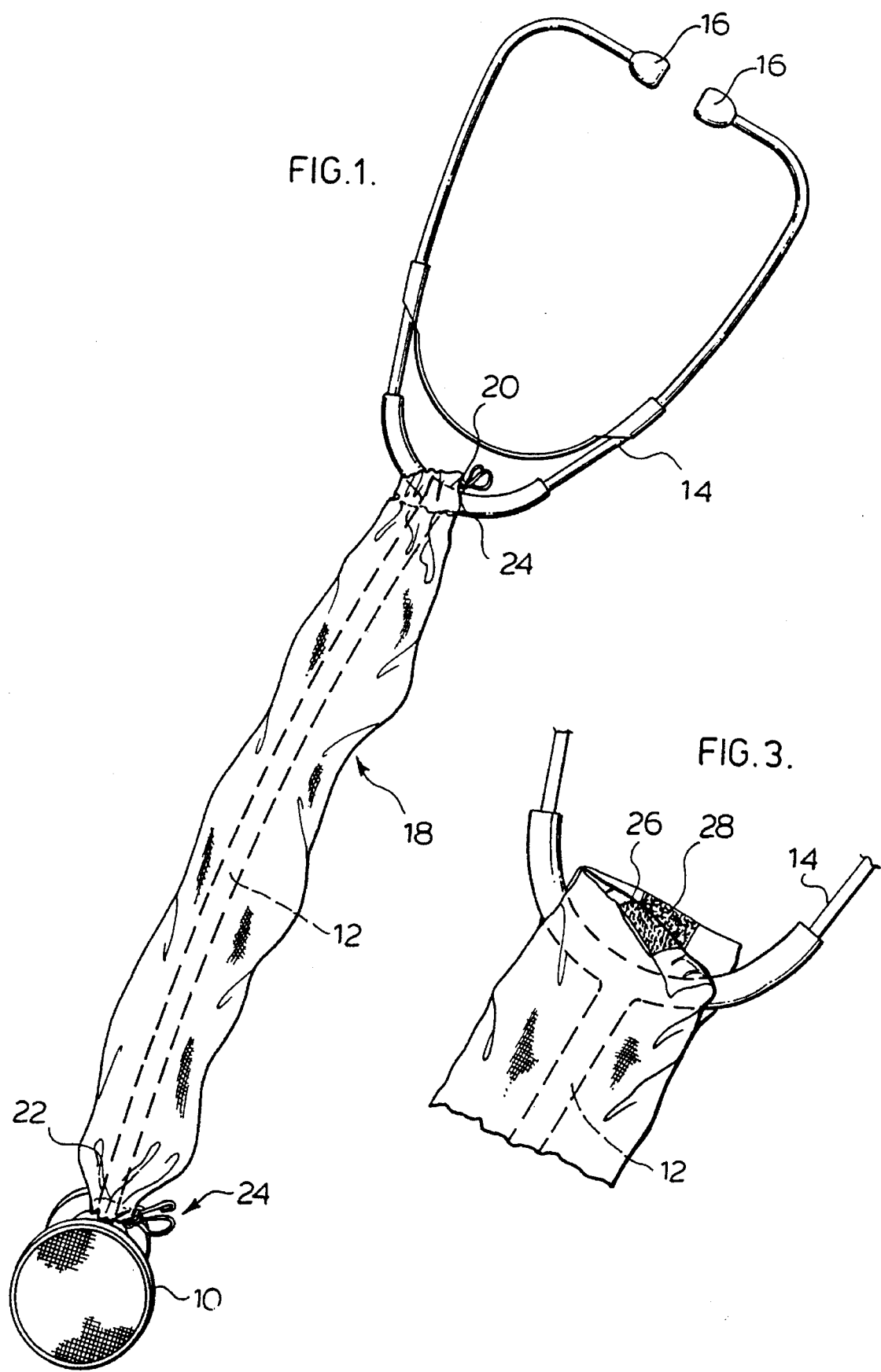

United States Patent [19]

Tuttle

[11] Patent Number: 5,539,162
[45] Date of Patent: Jul. 23, 1996

[54] STETHOSCOPE AND SLEEVE

[76] Inventor: Donna Tuttle, 98 Scarboro Avenue, Scarborough, Ontario, Canada, M1C 1M4

[21] Appl. No.: 345,983

[22] Filed: Nov. 28, 1994

[51] Int. Cl.⁶ .................................................. A61B 7/02
[52] U.S. Cl. ...................................................... 181/131
[58] Field of Search ............................ 181/131; 381/67; 128/715

[56] References Cited

U.S. PATENT DOCUMENTS 5,269,314 12/1993 Kendall et al. ...................... 181/131 X
5,466,898 11/1995 Gilbert et al. .......................... 181/131

Primary Examiner—Khanh Dang

[57] ABSTRACT

A stethoscope is combined with a cover, to cover the portion of the tubing which will contact the carrier's neck when the stethoscope is carried about the neck.

20 Claims, 2 Drawing Sheets

U.S. Patent  Jul. 23, 1996  Sheet 2 of 2  5,539,162

STETHOSCOPE AND SLEEVE

This invention relates to the combination of a stethoscope and a cover therefor.

A stethoscope comprises a head, eartubes, eartips and a single or double connecting tube. On a single tube stethoscope, the tubing bifurcates to form the eartubes. The main undivided extent of the tubing ends at the head or chestpiece. On a double tube stethoscope, the tubes lie side by side from the head to where they split to form the eartubes.

Thus by the term 'undivided extent' herein I include the single tube stethoscopes in the extent between the head and the bifurcation, and in the double tube stethoscope, the corresponding extent between the head and the eartubes.

The stethoscope is, when not in use, frequently worn about the neck of the user for extended periods of time. The user is often a nurse, doctor, ambulance attendant or paramedic. The tube is therefore exposed to the oils and sweat of the user and sometimes to splashed body substances and eventually tends to harden and deteriorate. Moreover the tube may be an irritant to the neck of the user.

In accord with this invention, I combine the conventional stethoscope with a sleeve which covers a length of the undivided extent of the tube and hence contacts the neck when worn thereabout. The sleeve may be of any material but will typically be of material which is a non irritant to user. The sleeve will preferably be made removable for cleaning or replacement.

I prefer to make the circumference of the sleeve sufficient to allow it to be applied to the undivided tube extent over the stethoscope head. The reasons are that on some stethoscopes the head is impossible or difficult of removal or replacement, while with other models the owner may not wish to remove the head, because of the risk of loss or damage.

If the head may be easily removed or replaced then it may be removed to allow application of the sleeve to the tube extent and the circumference of the sleeve need only be made great enough to be slidably applied to the undivided tube extent.

In a preferred variant of the invention the sleeve may be provided with a circumferential drawstring near one or both ends which can tighten the sleeve about the tube. The drawstring nearer the divided tube may be looped over one of the divided limbs to retain that end of the sleeve in place.

Although I prefer the use of drawstrings as discussed above, these can, if desired, be replaced by circumferential elastics adjacent one or both ends of the tube.

With circumferential drawstring where the sleeve is applied over the head, the drawstrings may be used to tighten the ends of the sleeve about the undivided tube after application thereto. This reduces any tendency of the sleeve to migrate along the undivided tube extent when in use.

With circumferential elastics, where the sleeve is applied over the head, the elastics will be selected to stretch to allow the passage of the sleeve over the head and are preferably dimensioned so that the elastic will tighten about the tube extent to inhibit migration of the sleeve.

Although not preferred, the sleeve may also be made as a flat sheet to be wrapped and fastened about the undivided extent of the tube.

It will also be noted that the most suitable material for the sleeve is thought to be fabric which may be machine tailored for mass production although I prefer to sew these by hand. It is however within the scope of the invention, although not preferred, to provide a sleeve of other material.

Figure 2:
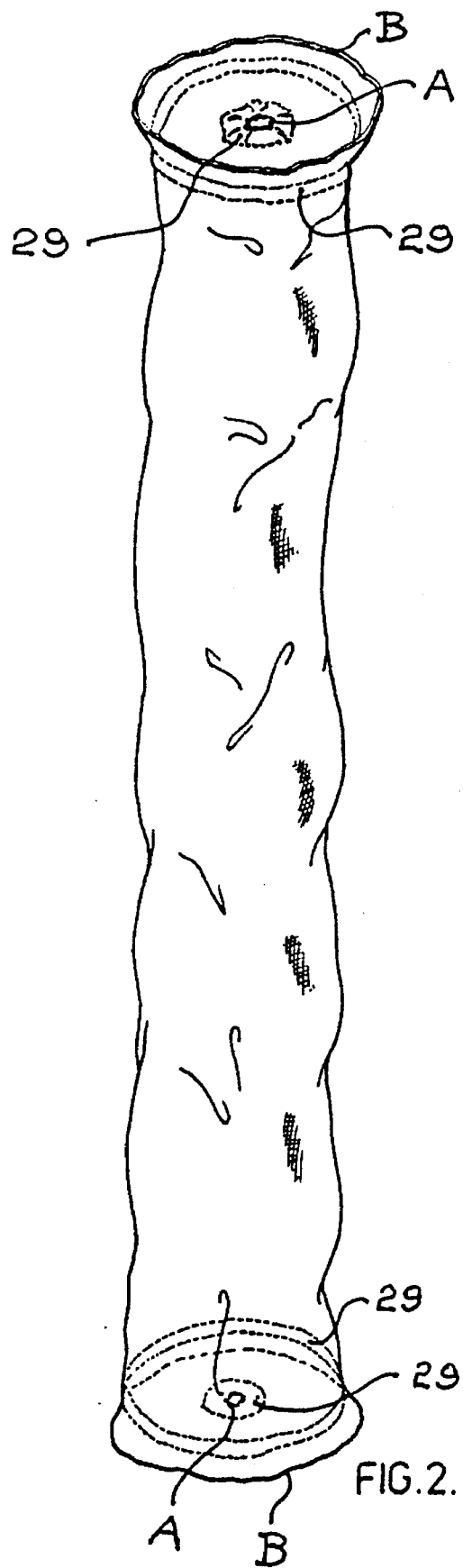
Figure 4:
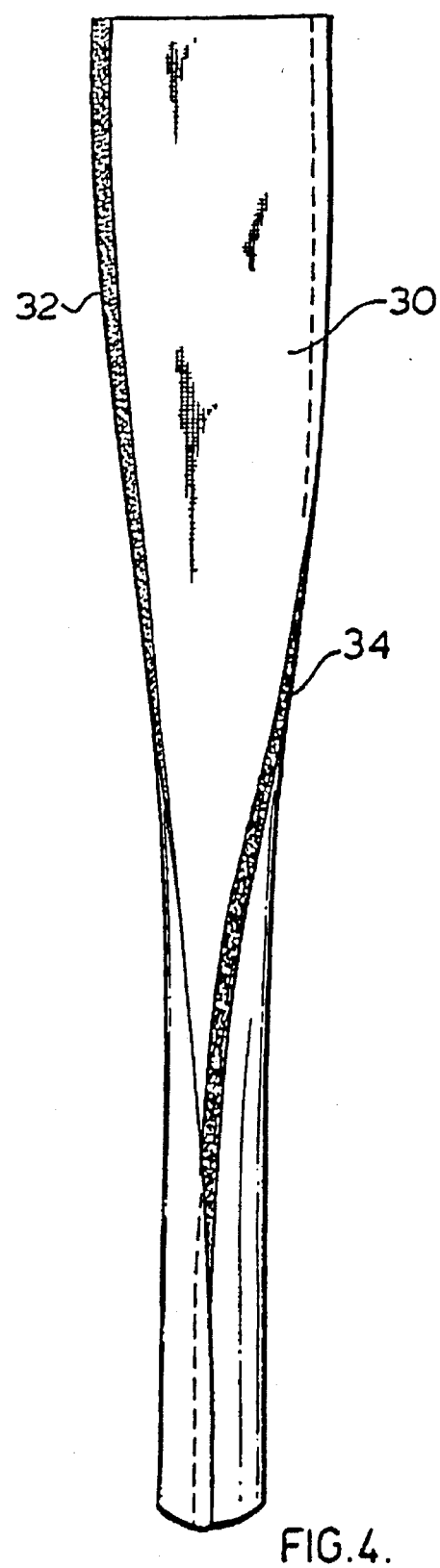

In drawings which illustrate a preferred embodiment of the invention:

FIG. 1 shows a fabric sleeve for use in combination with the stethoscope having drawstrings adjacent each end of the undivided tube extent, FIG. 2 shows the use of a circumferential elastic to replace the drawstring adjacent each end of the sleeve, FIG. 3 shows the use of a tab using hook and loop material to anchor one end of the sleeve, to the divided portion of the tube, and FIG. 4 shows a sleeve designed to be wrapped about the undivided tube extent.

In the description herein the sleeve may be thought of as having a 'circumference' running about the stethoscope tube and a 'length' running along the stethoscope tube. The terms 'circumference' or 'circumferential' on the one hand and 'length' or 'lengthwise' on the other hand are used with this in mind.

In FIG. 1 is shown a stethoscope having a head 10, an undivided tube extent 12, eartubes 14 and eartips 16.

In FIG. 1 a cotton sleeve 18 is shown surrounding the tube. At each end the fabric has been folded and sewn to provide a circumferential passage 20 for a drawstring 22 whose ends emerge at exits to allow a tie or knot 24 to gather the sleeve fabric at each end about the tube to tend to retain it in place.

It will be noted that the tube is shown as a single undivided tube split into two limbs but may be two tubes attached side by side in the undivided extent and splitting at the eartip end.

If desired, and as shown in FIG. 3 tabs 26 and 28 of complementary hook and loop material may be located on the inside of the sleeve at diametrically opposed locations near what is intended to be the eartube end of the tube extent 12 to fasten between the diverging eartubes.

Tabs 26 and 28 may be replaced by dome (or other) fasteners. If desired (although not shown) a sleeve may be provided both with drawstrings and tabs or other fasteners.

It is noted that any material comfortable to the wearer may be used. In addition to cotton fabric I have used other fabrics. The sleeve may be made of liquid proof or liquid absorbent material.

FIG. 2 is a view indicating that the drawstrings may be replaced by elastic 29 extending circumferentially at each end to yieldably gather the sleeve ends about the tube. FIG. 2 is intended to show the elastic in a distended circumference B to pass over the stethoscope head 10 and a contracted circumference A to gather the sleeve ends about the undivided extent, when in place thereon. Tabs 26 and 28 as shown in FIG. 2 or other fasteners may be combined with, the sleeve to fasten about the 'Y' of eartubes 14 to prevent migration of the sleeve.

Instead of the drawstrings or elastic of FIGS. 1 and 2, circumferentially acting hook and loop tabs may be used or any other gathering method may be used. The gathering at each end may be dispensed with, within the scope of the invention. If desired the drawstring, elastic or other fastening need only be provided at one end.

The length of the sleeve need not extend fully from the eartube bifurcation to the head but need only have a length to extend over the neck contacting portion of the tube, that is, over the majority of the undivided extent.

Most designs of the sleeve allow it to be stretched to be applied to the tube over the stethoscope head. However the head is removable from the tube in many instances and the sleeve, in this event, may be made of a smaller circumference slid lengthwise onto the tube. In such case the drawstrings or elastics may not be required.

The sleeve as described may be ornamented or ornamentally shaped as desired. For example I have sewn a sleeve, of greater length than required to a stretched lengthwise elastic (not shown) in such a manner that the sleeve when pulled by the lengthwise elastic presented a 'bunched' appearance.

FIG. 4 shows a sleeve design wherein the fabric is a sheet 30 having lengthwise strips 32 and 34 of complementary hook and loop material which may be fastened about the tube to form the sleeve. As shown the fabric and hook and loop material may be formed to provide a smaller circumference than sleeves which have to be passed over head 10. It must be emphasized however that I believe that this arrangement is not as satisfactory as the permanent circumferential arrangements of the type shown in FIGS. 1–3.

It is noted that the embodiments are directed to constructions which may be manually sewn. However, any mass production method may be used to produce sleeves in accord with the invention.

I claim:

1. In combination, a stethoscope and a sleeve:

said stethoscope comprising an undivided tube extent, a head connected to one end of said tube extent and two eartips connected to the other end of said tube extent through respective ear tubes, said sleeve surrounding a length of said undivided extent, said sleeve having an opening at one end, surrounding said tube extent, adjacent said head and an opening at the other end surrounding said tube extent adjacent said ear tubes, said sleeve surrounding said extent between said openings.

2. In combination as claimed in claim 1, wherein said sleeve is of a length to surround more than half of the length of said undivided extent.

3. In combination as claimed in claim 2, wherein said sleeve is designed to be applied to said tube over said head.

4. In combination as claimed in claim 1, wherein said sleeve includes a drawstring extending about one opening of said sleeve.

5. In combination as claimed in claim 2, wherein said sleeve includes a drawstring extending about one opening of said sleeve.

6. In combination as claimed in claim 1, wherein said sleeve includes an elastic extending about one of said openings.

7. In combination as claimed in claim 2, wherein said sleeve includes an elastic extending about one end of said openings.

8. In combination as claimed in claim 1, wherein said sleeve surrounds said undivided extent and means are provided to attach one end of said sleeve to one of said eartubes.

9. In combination as claimed in claim 2, wherein said sleeve surrounds said undivided extent and means are provided to attach one end of said sleeve to one of said eartubes.

10. In combination as claimed in claim 3, wherein said sleeve surrounds said undivided extent and means are provided to attach one end of said sleeve to one of said eartubes.

11. In combination as claimed in claim 4, wherein said sleeve surrounds said undivided extent and means are provided to attach one end of said sleeve to one of said eartubes.

12. In combination as claimed in claim 2 wherein said sleeve is capable of easy removal and replacement.

13. In combination as claimed in claim 12 wherein said head is readily detachable from and attachable to said tube extent, and wherein said sleeve is adapted to be slid onto said tube extent when the head is removed therefrom.

14. A combination as claimed in claim 1 wherein said sleeve is formed from a sheet of material wrapped about the tube.

15. With a stethoscope having an undivided tube extent, a head connected to one end of said extent and two ear pieces connected to the other end of said undivided tube extent through respective ear tubes, a method of covering a length of the undivided extent of said stethoscope tube, comprising the steps of:

providing a sleeve with an opening at each end dimensioned to cover more than half of said extent placing said sleeve about said extent with said extent extending through each of said openings.

16. A method as claimed in claim 15, wherein said sleeve is passed over the head of said stethoscope in placing it on said extent.

17. A method as claimed in claim 15, wherein said sleeve is provided with a drawstring surrounding each opening and said drawstrings are tightened and tied when said sleeve is on said extent.

18. A method as claimed in claim 16, wherein said sleeve is provided with a drawstring surrounding each opening and said drawstrings are tightened and tied when said sleeve is on said extent.

19. A method as claimed in claim 15, wherein an elastic extends about each sleeve opening and contracts about said tube.

20. A method as claimed in claim 16, wherein an elastic extends about each sleeve opening and contracts about said tube.

* * * * *